Figure 1:
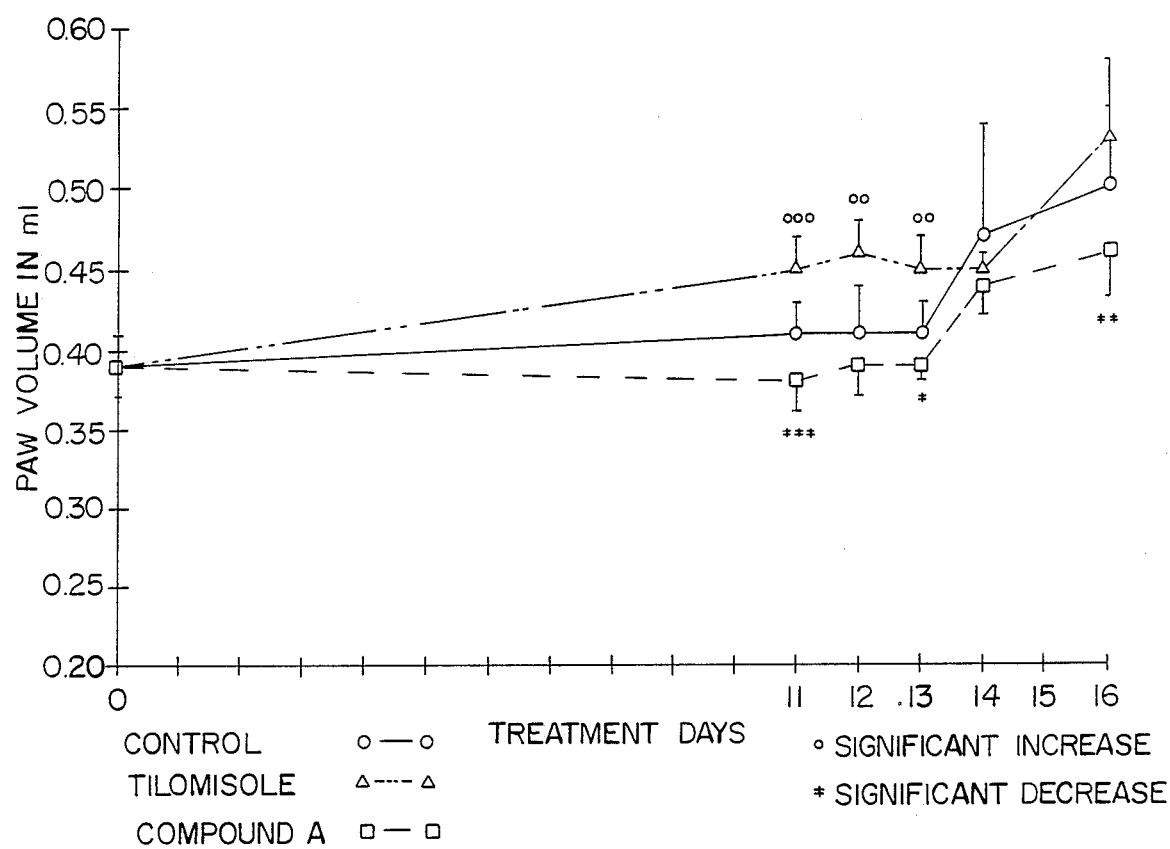

United States Patent [19]

Binder et al.

[11] Patent Number: 4,978,671
[45] Date of Patent: Dec. 18, 1990

[54] THIENO (3',4'-4,5)IMIDAZO(2,1-b)THIAZOLE DERIVATIVES, A PROCESS FOR THEIR PREPARATION AND THEIR USE IN MEDICAMENTS

[75] Inventors: Dieter Binder, Wien; Franz Rovenszky, Bruck a. d. Leitha; Hubert P. Ferber, Ansfelden, all of Austria

[73] Assignee: Chemisch Pharmazeutische Forschungsgesellschaft m.b.H., Linz, Austria

[21] Appl. No.: 401,135

[22] Filed: Aug. 30, 1989

[30] Foreign Application Priority Data

Sep. 8, 1988 [AT] Austria .................. 2202/88

[51] Int. Cl.$^5$ .................. C07D 513/14; A01K 31/425
[52] U.S. Cl. ...................... 514/366; 548/151
[58] Field of Search .................. 548/151; 514/366

[56] References Cited

U.S. PATENT DOCUMENTS

| 4,214,089 | 7/1980 | Fenichel | 548/151 |
| 4,244,952 | 1/1981 | Munakata et al. | 548/151 |
| 4,293,696 | 10/1981 | Wei et al. | 548/151 |

FOREIGN PATENT DOCUMENTS 284893 10/1988 European Pat. Off. ............ 548/151

OTHER PUBLICATIONS

Gilman et al., "Agents and Actions", vol. 17 (1), 53-59 (1985).
Dauben, "J. Org. Chem." 15, 785-789 (1950).
Outerquin, "Bull. Soc. Chem. Fr.", 5-6 159-163 (1983).

Primary Examiner—Robert Gerstl
Attorney, Agent, or Firm—Wenderoth, Lind & Ponack

[57] ABSTRACT

The invention relates to novel thieno-(3',4'-4,5)imidazo(2,1-b)thiazole derivatives of the formula

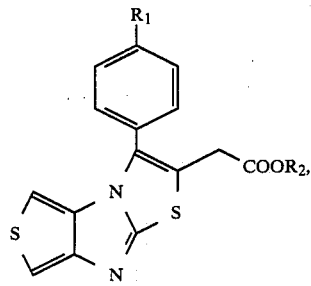

in which
$R_1$ denotes hydrogen, halogen or $CF_3$ and
$R_2$ denotes hydrogen or $C_1$-$C_4$ alkyl and, in the case in which $R_2$ denotes hydrogen, their pharmaceutically utilizable salts, a process for the preparation of these compounds and their use for the treatment of cancer or rheumatoid arthritis caused by a defective immune system.

5 Claims, 1 Drawing Sheet

THIENO (3',4'-4,5)IMIDAZO(2,1-b)THIAZOLE DERIVATIVES, A PROCESS FOR THEIR PREPARATION AND THEIR USE IN MEDICAMENTS

DESCRIPTION

The invention relates to thieno(3',4'-4,5)imidazo(2,1-b)thiazole derivatives, a process for their preparation and their use in medicaments for stimulating the immune system.

In Agents and Actions, Vol. 17, 1 (1985) S. C. Gilman et al. describe 3-(p-chlorophenyl)thiazolo(3,2-a)benzimidazole-2-acetic acid as an anti-inflammatory and immunomodulating substance.

It has now been found that thieno(3',4'-4,5)imidazo(2,1-b)thiazole derivatives have an improved pharmacological action compared to the prior art.

The invention therefore relates to compounds of the formula

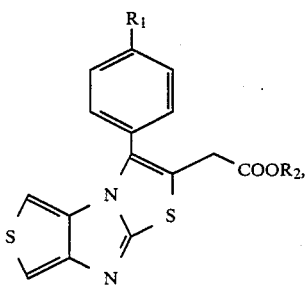

in which
  $R_1$ denotes hydrogen, halogen or trifluoromethyl and $R_2$ denotes hydrogen or $C_1$–$C_4$ alkyl, and, in the case in which
  $R_2$ denotes hydrogen, their pharmaceutically utilizable salts.

The expression "$C_1$–$C_4$ alkyl" used in this description signifies straight-chain or branched saturated hydrocarbon radicals having 1 to 4 carbon atoms, such as, for example, methyl, ethyl, propyl, isopropyl, butyl, isobutyl or tert. butyl. The expression "halogen" signifies chlorine, bromine or fluorine.

A prefered class of the compounds of the formula I is that in which $R_1$ denotes chlorine and $R_2$ denotes hydrogen or methyl.

Particularly preferred individual compounds are:
  Methyl 3-(4-chlorophenyl)-thieno(3',4'-4,5)imidazo(2,1-b)thiazole-2-acetate 3-(4-chlorophenyl)-thieno(3',4'-4,5)imidazo(2,1-b)thiazole-2-acetic acid The thieno(3',4'-4,5)imidazo(2,1-b)thiazole derivatives of the formula I and their salts are prepared according to the invention by a process in which
  (a) a compound of the formula

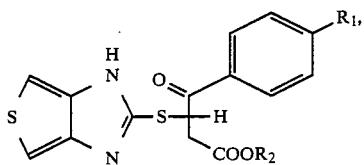

in which $R_1$ has the above meaning and $R_2$ is $C_1$–$C_4$ alkyl, or an acid addition salt thereof is cyclized in the presence of dehydrating reagents, whereupon (b) if desired, a compound of the formula I thus obtained, in which $R_2$ denotes $C_1$–$C_4$ alkyl, is hydrolyzed under alkaline conditions to give a compound of the formula I, in which $R_2$ denotes hydrogen, and (c) if desired, a free acid of the formula I, in which $R_2$ denotes hydrogen, obtained in process step b) is converted to a pharmaceutically tolerable salt using inorganic or organic bases.

All customarily used dehydrating agents can be used as dehydrating reagents in the cyclization of compounds of the formula II. Polyphosphoric acid or phosphorus oxychloride, which can be used at the same time as a solvent, are preferred. The cyclization temperature should be about 60° C. to 110° C. In phosphorus oxychloride, the cyclization is best carried out at reflux temperature. The reaction time, depending on the temperature and the cyclization agent, is between about 10 minutes and 4 hours.

If desired, the esters of the formula I can be hydrolyzed by boiling with bases, preferably using equivalent amounts of alkali metal hydroxide solutions and advantageously with the addition of a solubilizer such as, for example, methanol or ethanol, to give compounds of the formula I, in which $R_2$ denotes hydrogen in nearly quantitative yields.

The compounds of the formula I which have a free carboxyl group obtained in the reaction in process step b) can be converted into their pharmaceutically utilizable salts in a customary manner using inorganic or organic bases. Salt formation can be carried out, for example, by dissolving the compounds of the formula I mentioned, in which $R_2$ denotes hydrogen, in a suitable solvent, such as, for example, water or a lower aliphatic alcohol, adding an equivalent amount of the desired base, ensuring thorough mixing and, after completion of salt formation, distilling off the solvent in vacuo. If desired, the salts can be recrystallized after isolation.

Pharmaceutically utilizable salts can be metal salts, in particular, alkali metal or alkaline earth metal salts, such as sodium salts, potassium salts, magnesium salts or calcium salts. Other pharmaceutically utilizable salts are also, for example, easily crystallizing ammonium salts. The latter are derived from ammonia or organic amines, for example, mono-, di- or tri-lower-(alkyl, cycloalkyl or hydroxyalkyl)amines, lower alkylenediamines or (hydroxy lower alkyl or aryl lower alkyl) lower alkyl ammonium bases, for example methylamine, diethylamine, triethylamine, dicyclohexylamine, triethanolamine, ethylenediamine, tris(hydroxymethyl) aminomethane, benzyl-trimethylammonium hydroxide and the like.

Starting from the compounds of the formulae III known from the literature (F. Outerquin and C. Paulmier, Bull. Soc. Chim. Fr., 5–6, 159–163 (1983)) and V (W. G. Dauben, H. Tilles, J. Org. Chem. 15, 785–789 (1950)), the compounds of the general formula II can be synthesized according to the following equation by customary chemical working methods familiar to any person skilled in the art:

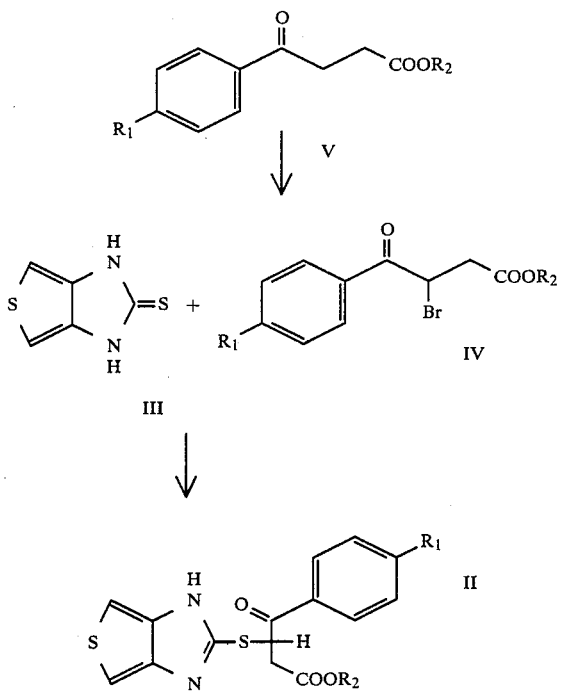

The novel compounds of the formula I and their pharmaceutically utilizable salts show an excellent stimulation of the immune system of in vitro models. This stimulation of the immune system can be measured, for example, by measurement of the anti-inflammatory activity of the test substances in the adjuvant-induced rat polyarthritis test.

In this test system, the anti-inflammatory action of the substance of Example 2 of the present application (compound A) was compared with 3-(4-chlorophenyl)-thiazolo(3,2-a)benzimidazole-2-acetic acid (tilomisole) (Example 3). From this comparison, it can be seen that the compound of the present invention is clearly superior to tilomisole.

On the basis of these pharmacological properties, the novel compounds can be used as medicaments alone or mixed with other active substances in the form of customary galenical preparations in disorders which are caused by a defective immune system, such as, for example, cancer or rheumatoid arthritis.

The compounds of the formula I are intended for use in humans and can be administered in a customary manner, such as, for example, orally or parenterally. They are preferably administered orally, the daily dose being 0.1 to 100 mg/kg of body weight, preferably 0.2 to 20 mg/kg of body weight. The treating physician can also prescribe doses above or below this, however, depending on the general state and age of the patient, the appropriate substance of the formula I, the nature of the disease and the manner of formulation.

If the substances according to the invention are for prophylactic use, the doses are approximately on the same scale as in the treatment case. Oral administration is also preferred in the case of prophylaxis.

The compounds of the formula I can be administered alone or in combination with other pharmaceutically active substances, the content of the compounds of the formula I being between 0.1 % and 99%. In general, the pharmaceutically active compounds are present mixed with suitable inert auxiliaries and/or excipients or diluents, such as, for example, pharmaceutically acceptable solvents, gelatine, gum arabic, lactose, starch, magnesium stearate, talc, vegetable oils, polyalkylene glycol, petroleum jelly and the like. The pharmaceutical preparations may be present in solid form, for example as tablets, coated tablets, suppositories, capsules and the like, in semi-solid form, for example as ointments or in liquid form, for example as solutions, suspensions or emulsions. If appropriate, they are sterilized and contain auxiliaries, such as preservatives, stabilizers or emulsifiers, salts for altering the osmotic pressure and the like.

Pharmaceutical preparations may in particular contain the compounds according to the invention in combination with other therapeutically useful substances. The compounds according to the invention can be formulated with these, for example, together with the abovementioned auxiliaries and/or excipients or diluents, to give combination preparations.

EXAMPLE 1

Methyl 3-(4-chlorophenyl)thieno(3',4'-4,5)imidazo(2,1-b)thiazole-2-acetate 8.00 g (17.3 mmol) of 4-(4-chlorophenyl)-4-oxo-3-(1H-thieno(3,4-d)-imidazol-2-yl)thiobutanoic acid methyl ester hydrobromide are suspended in 75 ml of phosphorus oxychloride and heated to boiling for 10 minutes. The excess phosphorus oxychloride is removed by distillation and the residue is neutralized using saturated sodium hydrogen carbonate solution. The mixture is then extracted three times with a total of 500 ml of ethyl acetate. The combined organic phases are dried over sodium sulphate, filtered and evaporated. The residue is recrystallized from acetone.

Yield: 2.00 g (31.8% of theory),
m.p.: 188°–190° C. (acetone),
$^1$H-NMR: (DMSO): delta (ppm): 7.68 (s, 4H, Ph—H); 7.22; 7.19; 6.54; 6.51 (AB, 2H, Th—H); 3.81 (s, 2H, —CH$_2$—COO—),3.67(s, 3H,—COOCH$_3$), The starting material can be prepared as follows:

Methyl 3-bromo-4-(4-chlorophenyl)-4-oxobutanoate 50.0 g (0.221 mol) of methyl 4-(4-chlorophenyl)-4-oxobutanoate (C. F. H. Allen, J. B. Normington and C. V. Wilson, Can. J. Research 11, 382 (1934)) are dissolved in 250 ml of glacial acetic acid and three drops of a solution of hydrogen bromide in glacial acetic acid are added. 35.3 g (0.221 mol) of bromine are added dropwise with stirring in such a way that no noticeable brown colouration can be formed in the reaction mixture. After completion of the addition, the mixture is additionally stirred for 15 minutes. The acetic acid is then largely removed by distillation. The residue is neutralized with saturated sodium hydrogen carbonate solution and extracted three times with a total of 600 ml of methylene chloride. The combined organic phases are dried over sodium sulphate, filtered and evaporated (67.2 g of yellow oil). The latter is rubbed with methanol and recrystallized from methanol.

Yield: 65.2 g of colourless crystals (97% of theory),
m.p.: 48°–49° C. (methanol), 4-(4-chlorophenyl)-4-oxo-3-(1H-thieno(3,4-d)imidazol-2-yl)thio-butanoic acid methyl ester hydrobromide 4.00 g (25.6 mmol) of 1,3-dihydrothieno(3,4-d)imidazole-2-thione and 7.11 g (23.3 mmol) of methyl 3-bromo-4-(4-chlorophenyl)-4-oxobutanoate are dissolved in 100 ml of absolute methanol and heated under reflux for 1.5 hours. About 1 g of active carbon is then added to the solution, which is filtered and evaporated. The residue obtained is digested with diethyl ether.

Yield: 9.10 g of beige crystals (84.6% of theory), m.p.: 180°–185° C. dec. (acetone),

EXAMPLE 2

3-(4-chlorophenyl)thieno(3',4'-4,5)imidazo(2,1-b)thiazole-2-acetic acid 2.00 g (5.51 mmol) of methyl 3-(4-chlorophenyl)-thieno(3',4'-4,5)imidazo(2,1-b)thiazole-2-acetate are suspended in 20 ml of methanol, 3 ml of 2N aqueous sodium hydroxide solution are added and the mixture is heated under reflux for 15 minutes. The reaction mixture is concentrated to about 10 ml and acidified with 2N hydrochloric acid. The precipitated product is filtered off with suction, washed three times with distilled water and recrystallized from methanol.

Yield: 1.50 g of colourless crystals (78% of theory), m.p.: 200°–210° C. dec. (methanol), $^1$H-NMR: (DMSO) delta (ppm): 8.87 (s, broad, 1H, —COOH) 7.72 (s, 4H, Ph-H); 7.42; 7.39; 6.77; 6.74 (AB, 2H, Th—H); 3.83 (s, 2H, —CH$_2$—COO—).

EXAMPLE 3

Investigation of the immunomodulating effect in the adjuvant-induced rat polyarthritis test The pharmacological effect of 3-(4-chlorophenyl)-thieno(3',4'-4,5)-imidazo(2,1-b)thiazole-2-acetate (compound A, =the compound of Example 2 of the present application) was measured in the adjuvant-induced rat polyarthritis test in comparison with 3-(4-chlorophenyl)thiazolo(3,2-a)benzimidazole-2-acetate (tilomisole, compound B).

In this test, the experimental substances were administered intraperitoneally in a concentration of 10 mg/kg of body weight daily over a period of 16 days to female Lewis rats which have an inborn immune defect. 6 animals were employed with each substance. Animals which received 0.5% carboxymethylcellulose instead of the active substance were used as controls. On day zero (i.e. one day before the beginning of the administration of the experimental substances), a subplantar injection of 0.75 mg of Mycobacterium butyricum in 0.1 ml of Freund's adjuvant was made in the right foot of each experimental animal. From the 11th–14th day, a secondary reaction took place in the left foot, which was not injected, which was manifested by a swelling of the foot. Since this swelling is caused by an immune reaction, substances which reduce this genetically conditioned and morbid reaction are designated as immunomodulators. The size of the swelling was measured daily by plethysmometry and indicated in ml.

The results of this experiment are summarized in Table 1 and FIG. 1.

TABLE 1

| | Foot volume in ml | | |
|---|---|---|---|
| Day | Control (0.5% CMC) | Tilomisole 10 mg/kg i.p. | Compound A 10 mg/kg i.p. |
| 0 | 0.39 ± 0.02 | 0.39 ± 0.02 | 0.39 ± 0.02 |
| 11 | 0.41 ± 0.02 | 0.45 ± 0.02°°° | 0.38 ± 0.02 ** |
| 12 | 0.41 ± 0.03 | 0.46 ± 0.02°° | 0.39 ± 0.02 |
| 13 | 0.41 ± 0.02 | 0.45 ± 0.02°° | 0.39 ± 0.01 * |
| 14 | 0.47 ± 0.07 | 0.45 ± 0.01 | 0.44 ± 0.02 |
| 16 | 0.50 ± 0.05 | 0.53 ± 0.05 | 0.46 ± 0.03 * |

°significant increase
*significant decrease
CMC: Carboxymethylcellulose

As can be seen from Table 1 and FIG. 1, only compound A inhibits the secondary reaction going back to the immune reaction at all points in time investigated.

What we claim is:

1. A compound of the formula

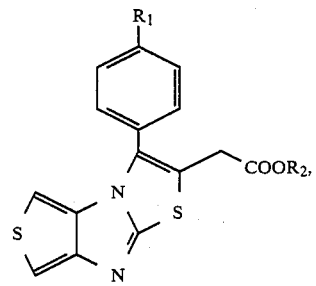

in which R$_1$ denotes hydrogen, halogen or CF$_3$ and R$_2$ denotes hydrogen or C$_1$–C$_4$ alkyl and, in the case in which R$_2$ denotes hydrogen, their pharmaceutically utilizable salts.

2. The compound of the formula I according to claim 1 and salt thereof, in which R$_1$ denotes chlorine and R$_2$ denotes hydrogen or methyl.

3. Methyl 3-(4-chlorophenyl)-thieno(3',4'-4,5)imidazo(2,1-b)thiazole-2-acetate. 3-(4-chlorophenyl)-thieno(3',4'-4,5)imidazo(2,1-b)thiazole-2-acetic acid.

4. The pharmaceutical composition comprising a compound of formula I or a salt thereof as claimed in claim 1 in an amount effective for the treatment of rheumatoid arthritis in combination with a pharmaceutically acceptable carrier or diluent.

5. A method for the treatment of rheumatoid arthritis which comprises administering an effective amount of a compound of formula I or a salt thereof as claimed in claim 1 to a patient suffering from rheumatoid arthritis.

* * * * *